United States Patent
Riondel

(10) Patent No.: US 6,670,508 B2
(45) Date of Patent: Dec. 30, 2003

(54) PROCESS FOR MANUFACTURING THE CHLORIDE OF 1,3-BIS-(DIMETHYLBENZYLAMMONIUM) ISOPROPYL, ACRYLATE ALONE OR MIXED WITH OTHER MONOMERS, AND CORRESPONDING (CO) POLYMERS

(75) Inventor: Alain Riondel, Forbach (FR)

(73) Assignee: Atofina, Puteaux (FR)

(*) Notice: Subject to any disclaimer, the term of this patent is extended or adjusted under 35 U.S.C. 154(b) by 21 days.

(21) Appl. No.: 10/132,691

(22) Filed: Apr. 26, 2002

(65) Prior Publication Data

US 2002/0193545 A1 Dec. 19, 2002

(30) Foreign Application Priority Data

Apr. 26, 2001 (FR) .............................. 01 05610

(51) Int. Cl.$^7$ ............................ C07C 211/00
(52) U.S. Cl. ............... 564/282; 524/555; 524/815; 526/312; 526/328.5; 560/221; 560/222
(58) Field of Search .................. 524/555, 815; 526/312, 328.5; 564/282; 560/221, 222

(56) References Cited

U.S. PATENT DOCUMENTS

| 5,912,383 A | 6/1999 | Riondel et al. | |
|---|---|---|---|
| 2002/0035198 A1 * | 3/2002 | N'Zudie et al. | 524/555 |
| 2002/0183543 A1 * | 12/2002 | Riondel et al. | 560/217 |
| 2003/0023113 A1 * | 1/2003 | Druzkowski et al. | 560/222 |

FOREIGN PATENT DOCUMENTS

| DE | 3048 020 A1 | 7/1982 |
|---|---|---|
| EP | 0 250 325 A2 | 12/1987 |
| EP | 0281 718 A2 | 9/1988 |
| EP | 0 329 512 A | 8/1989 |
| EP | 0420790 A1 | 4/1991 |
| EP | 0 428 970 A | 5/1991 |
| EP | 0663386 A1 | 7/1995 |
| EP | 0930 290 A1 | 7/1999 |
| FR | 1 529 000 A | 10/1968 |
| FR | 2 027 225 | 9/1970 |
| FR | 2 707 291 | 1/1995 |
| FR | 2 788 767 | 7/2000 |
| WO | WO 89/07588 | 8/1989 |

OTHER PUBLICATIONS

Abstract of JP 07 238057 A, Sep. 12, 1995.
Abstract of JP 10 072433 A, Mar. 17, 1998.

* cited by examiner

*Primary Examiner*—Helen L. Pezzuto
(74) *Attorney, Agent, or Firm*—Millen White Zelano & Branigan, P.C.

(57) ABSTRACT

A compound of formula (I) is prepared alone or in combination with at least one monomer of formula (II): the quaternizing agents benzyl chloride is introduced into a solution, in a solvent selected from compounds of the formulae (I) and (II) and mixtures of these, of the compound of formula (III) at a temperature of from 35 to 60° C., and then water is added and the reaction is allowed to proceed to complete or substantially complete conversion of the compound (III), an aqueous solution of desired compound (I) is isolated where appropriate with at least one compound (II), if this or these have/has been used as solvent, and the water is removed where appropriate.

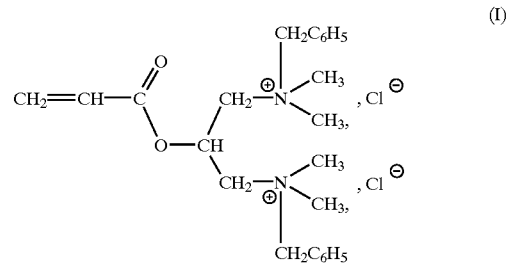

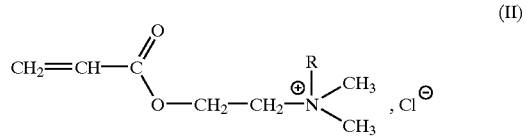

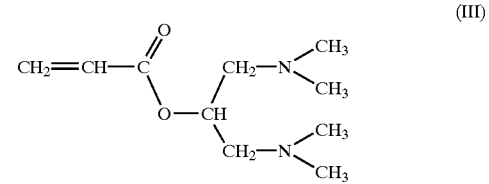

13 Claims, No Drawings

PROCESS FOR MANUFACTURING THE CHLORIDE OF 1,3-BIS-(DIMETHYLBENZYLAMMONIUM) ISOPROPYL, ACRYLATE ALONE OR MIXED WITH OTHER MONOMERS, AND CORRESPONDING (CO) POLYMERS

CROSS-REFERENCE TO RELATED APPLICATIONS

The present application is related to U.S. application Ser. No. 10/132,739, filed Apr. 26, 2002 based on French priority application No. 01.05609 filed Apr. 26, 2001, and U.S. application Ser. No. 10/132,690, filed Apr. 26, 2002 based on French priority application No. 01.05701, filed Apr. 27, 2001.

The present invention relates to the monomer of formula (I) having two quaternary amino groups:

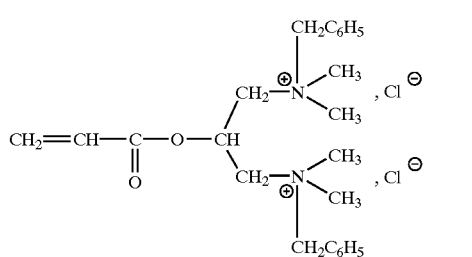

this being the chloride of 1,3-bis(dimethylbenzyl-ammonium)isopropyl acrylate (also known by the abbreviated term S-ADAMQUAT 2 BZ).

Patent Application No. 00-00834 filed on Jan. 24, 2000 entitled "Procédé de fabrication de monomères à deux groupes amino quaternaires et les (co)polymères obtenus à partir de ces monomères" [Process for manufacturing monomers having two quaternary amino groups and the (co)polymers obtained from these monomers] discloses the preparation of the monomer of formula (I) in aqueous solution by the process consisting in introducing the quaternizing agent benzyl chloride into a solution, in chloroform, dichloromethane or dichloroethane, of (2-dimethylamino-1-dimethylaminomethyl)ethyl acrylate (also known by the abbreviated term S-ADAME), at a temperature of from 35 to 80° C., the reaction then being permitted to proceed at the said temperature to complete or substantially complete consumption of the S-ADAME, and an aqueous solution of this compound then being isolated, with the option to remove the water where appropriate.

The French Patent Application No. 00-00833, filed Jan. 24, 2000 and entitled "Dispersions aqueuses sans sel de copolymères hydrosolubles à base de monomères cationiques, leur procédé de fabrication et leurs applications" [Salt-free aqueous dispersions of water-soluble copolymers based on cationic monomers, process for their manufacture, and their applications] discloses a salt-free aqueous dispersion of a water-soluble copolymer obtained from a composition of monomers comprising, for 100 molar parts:

(a) from 0.5 to 99.5 molar parts of at least one monomer which may be S-ADAMQUAT 2BZ; and
(b) from 99.5 to 0.5 molar parts of at least one monomer which may be selected, inter alia, from acryloxyethyltrimethylammonium chloride (ADAMQUAT MC) and acryloxyethyldimethylbenzyl-ammonium chloride (Adamquat BZ);

where the said composition of monomers may include, for 100 molar parts of (a)+(b):

(c) up to 30 molar parts of at least one hydrophobic monomer; and/or
(d) up to 10 molar parts of at least one crosslinking monomer; and/or
(e) up to 30 molar parts of at least one amphiphilic monomer.

These salt-free aqueous dispersions in particular comprise, for 100 parts by weight:

(A) from 5 to 50 parts by weight of dispersed copolymer based on the composition of monomers (a) to (e) defined above; and
(B) from 0.5 to 25 parts by weight of at least one dispersant (co)polymer, the remainder being water.

They are manufactured by aqueous free-radical polymerization of the monomer(s) (a) to (e) as defined above in the presence of the polymer dispersant(s) (B), and they are used as flocculators for treating aqueous effluent; fibre-retention agents and fillers in papermaking processes; agents facilitating the cleaning of media, such as textile; agents for filler dispersion; agents for inhibiting the transfer of pigments and colorants on various media, such as textile, thickeners, and dehydrators.

French Patent Application No. 00-00832, filed Jan. 24, 2000 and entitled "Dispersions aqueuses salines de (co) polymères hydrosolubles à base de monomères cationiques, leur procédé de fabrication et leurs applications" [Saline aqueous dispersions of water-soluble (co)polymers based on cationic monomers, process for their manufacture, and their applications] discloses a saline aqueous dispersion of a water-soluble (co)polymer obtained from a composition of water-soluble monomers comprising, for 100 molar parts:

(1) from 2 to 100 molar parts of at least one monomer which may be S-ADAMQUAT 2BZ; and
(2) from 0 to 95 molar parts of at least one monomer which may be selected, inter alia, from acryloxyethyltrimethylammonium chloride (ADAMQUAT MC) and acryloxyethyldimethylbenzyl-ammonium chloride (Adamquat BZ);

where it is possible for other monomers (2) to (5) described in that French patent application also to be present, including monomer (3):

(3) from 0 to 95 molar parts of at least one monomer which may be selected, inter alia, from acryloxyethyltrimethylammonium chloride (ADAMQUAT MC) and acryloxyethyldimethylbenzyl-ammonium chloride (Adamquat BZ).

These saline aqueous dispersions in particular comprise, for 100 parts by weight:

(A) from 10 50 parts by weight of dispersed (co)polymer based on the composition of the said monomers (1) to (5);
(B) from 0.5 to 25 parts by weight of at least one dispersant (co)polymer; and
(C) from 10 to 45 parts by weight of at least one inorganic salt such that the aqueous solution dissolves the dispersant (co)polymer without dissolving the dispersed (co) polymer formed in the course of polymerization, the remainder being water.

They are manufactured by aqueous saline free-radical polymerization of the monomer(s) (1) to (5) in the presence of the polymer dispersant(s) (B) and the said inorganic salt(s) (C), and they are used as flocculators for treating aqueous effluent; dehydrators; fibre-retention agents and fillers in papermaking processes; agents facilitating the cleaning of media, such as textile; agents for filler dispersion; agents for inhibiting the transfer of pigments and colorants on various media, such as textile, and thickeners.

French Patent Application No. 00-00835, filed Jan. 24, 2000 and entitled "Dispersions aqueuses salines de copolymères hydrosolubles à base de monomères cationiques, leur procédé de fabrication et leurs applications" [Saline aqueous dispersions of water-soluble copolymers based on cationic monomers, process for their manufacture, and their applications] describes compositions likewise based on S-ADAMQUAT-2BZ, on ADAMQUAT MC and on ADAMQUAT BZ.

Now, it appears that the current process for synthesizing S-ADAMQUAT 2BZ is not capable of cost-effective industrial use. Furthermore, since it involves the presence of a solvent, the environmental situation is not ideal (VOCs problem).

Therefore, a solution to this double problem has been discovered that, surprisingly, the use of at least one of ADAMQUAT BZ, ADAMQUAT MC and S-ADAMQUAT 2BZ instead of chloroform or methylene chloride which are used currently permits the reaction time to be reduced and thus increases productivity by at least a factor of two, while removing the environmental constraint related to the solvent.

An object of the present invention, therefore, is a process for the manufacture of the compound of formula (I):

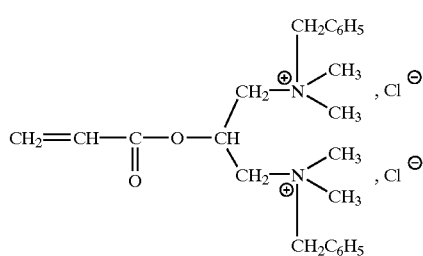

(I)

alone or in combination with at least one monomer of formula (II):

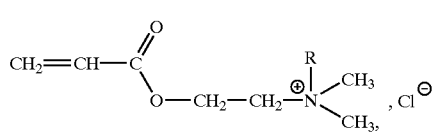

(II)

in which R represents —CH$_3$ or —CH$_2$C$_6$H$_5$,
characterized in that the benzyl chloride quaternizing agent is introduced into a solution, in a solvent selected from the compounds of the formulae (I) and (II) and mixtures of these, of the compound of the formula (III):

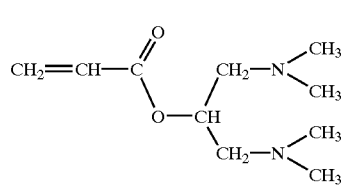

(III)

at a temperature of from 35 to 60° C., in particular from 40 to 50° C., and then water is added and the reaction is allowed to proceed to complete or substantially complete conversion of the compound (III), and that an aqueous solution of desired N-hydroxyethylethylenediaminetriacetate. The sequestering agents are generally added in the form of an aqueous solution, because they are generally available in that form. Thus, pentasodium diethylenetriaminepentaacetate marketed as VERSENEX 80 takes the form of an aqueous solution of about 40% by weight strength.

Depending on the circumstances, the process according to the invention leads to an aqueous solution of compound (I) solely, a concentration of compound (I) being from 50 to 75% by weight, or leads to an aqueous solution of compounds (I) and (II), the composition of the aqueous solution being the following, for 100 parts by weight:

| compound (I): | from 10 to 70% by weight |
|---|---|
| compound(s) (II): | from 10 to 70% by weight |
| water: | from 20 to 80% by weight |

These solutions may be used for polymerization directly or mixed with other comonomers.

Another object of the present invention is homopolymers or copolymers containing units of monomer (I) and where appropriate at least one unit monomer (II), where this or these monomer(s) has/have been obtained by the process defined above. Thus, the homopolymer or copolymer is made respectively from monomer I or monomers I and II.

These polymers may be water-soluble or hydrophobic polymers in the form of aqueous dispersion, latex, aqueous solution, inverse emulsion, or powder. They are prepared by free-radical copolymerization in accordance with various synthetic processes, such as polymerization processes in dispersion, solution, direct emulsion, inverse emulsion or inverse suspension.

The example below illustrates the present invention, but does not limit its scope. The parts and percentages given in this example are by weight unless otherwise indicated, and the following abbreviations have been used:

| S-ADAME: | (2-dimethylamino-1-dimethylaminomethyl)ethyl acrylate; |
|---|---|
| ADAMQUAT BZ 80: | 80% strength by weight solution of acryloxyethyldimethylbenzylammonium chloride; |
| S-ADAMQUAT 2BZ: | chloride of 1,3-bis(dimethylbenzyl-ammonium)isopropyl acrylate; |
| EMHQ: | methyl ether of hydroquinone |
| CBY1: | benzyl chloride |

EXAMPLE

Synthesis of S-ADAMQUAT 2BZ by quaternization of S-ADAME

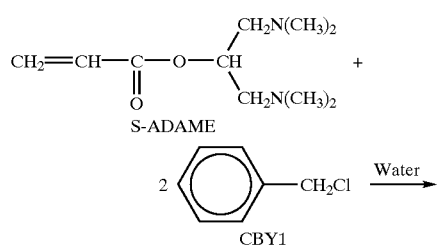

-continued

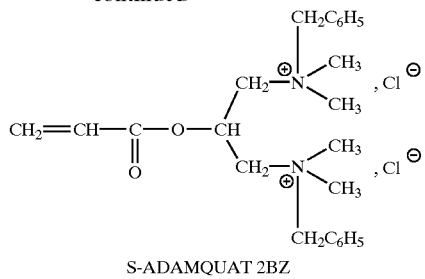

S-ADAMQUAT 2BZ 60 g of S-ADAME stabilized by 800 ppm of EMHQ and 93.2 g of ADAMQUAT BZ 80 stabilized by 400 ppm of EMHQ are charged to a 500 ml glass reactor, where, generally, S-ADAME is the solute and ADAMQUAT BZ80 is the solvent. Air is bubbled through the stirred mixture, which is brought to 50° C. 72.9 g of CBY1 (i.e. 24.3 g/h) of CBY1 are then added within 3 hours. Once 48.6 g of CBY1 have been introduced, corresponding to reaction for 2 hours, addition of 50.5 g of water within 4 hours (i.e. 12.6 g/h) is begun.

Once the introduction of water has been terminated, stirring compound (I) is isolated where appropriate with at least one compound (II) if this or these have/has been used as solvent, and that where appropriate the water is removed. Optionally, the process of the present invention can be carried out at atmospheric pressure. The reaction is conducted under such operating conditions so polymerisation does not occur. Preferably, the reaction is carried out at 35–60° C. because there is a tendency at temperatures above 60° C. towards polymerisation, although conditions can be altered, e.g., adding polymerisation inhibitors or adjusting stoichmetric ratios, to overcome this tendency. Likewise, there is a tendency for no reaction to occur below 35° C., although conditions can be altered, e.g., adding catalysts, to overcome this tendency.

The reaction is advantageously conducted with a molar ratio compound (III)/benzyl chloride of between 1.6 and 2.0, particularly between 1.7 and 1.9. The benzyl chloride is generally introduced into the solution of the compound (III) over a period of from 8 to 16 hours, the water is generally introduced into the solution of the compound (III) over a period of from 2 to 6 hours, and the introduction of the water is generally begun when from 10 to 80% of the benzyl chloride have been introduced.

The process is also advantageously conducted in the presence of at least one stabilizer selected from the methyl ether of hydroquinone, hydroquinone, 3,5-di-tert-butyl-4-hydroxytoluene and mixtures of these, in particular in a proportion of from 200 to 2 000 ppm, based on the final aqueous solution, and/or in the presence of at least one agent for sequestering metals, in particular in a proportion of from 10 to 100 ppm, based on the final aqueous solution.

The agents for sequestering metals are in particular selected from diethylenetriaminepentaacetic acid, pentasodium diethylenetriaminepentaacetate, N-hydroxyethylethylenediaminetriacetic acid and trisodium of the mixture is continued for a further 3.5 hours to complete conversion of the S-ADAME.

After cooling and discharge of the reactor, 252 g of product are obtained and comprise:

| | |
|---|---|
| $H_2O$ | 19% |
| ADAMQUAT BZ | 29% |
| S-ADAMQUAT 2BZ | 52% |

The mixture thus obtained is used for water-in-water polymerization for applications in the flocculant sector.

The preceding examples can be repeated with similar success by substituting the generically or specifically described reactants and/or operating conditions of this invention for those used in the preceding examples.

The entire disclosure of all applications, patents and publications, and of corresponding French Application No. 01.05610, filed Apr. 26, 2001, is hereby incorporated by reference.

From the foregoing description, one skilled in the art can easily ascertain the essential characteristics of this invention and, without departing from the spirit and scope of the thereof, can make various changes and modifications of the invention to adapt it to various usages and conditions.

What is claimed is:

1. A process for producing a compound of formula (I):

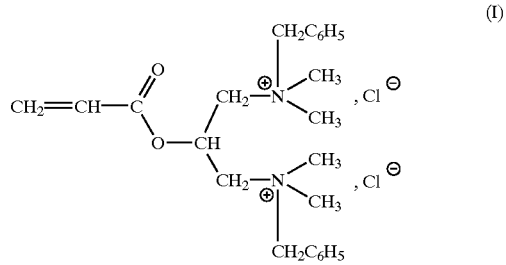

alone or in combination with at least one monomer of formula (II):

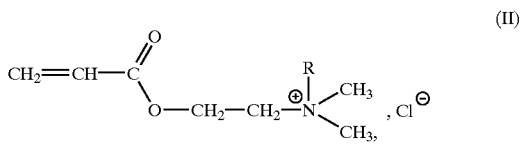

in which R represents —$CH_3$ or —$CH_2C_6H_5$, comprising introducing a benzyl chloride quaternizing agent into a solution, in a solvent of the compound of formula (I), formula (II), or a mixture thereof, and of a compound of formula (III):

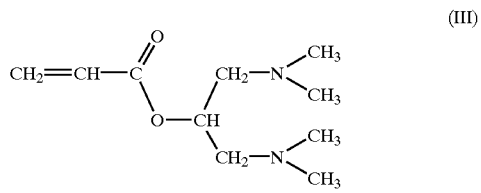

at a temperature 35–60° C., and then adding water and allowing the reaction to proceed to complete or substantially complete conversion of the compound (III), and isolating an aqueous solution of desired compound (I) optionally with at least one compound (II) if this or these have/has been used as solvent, and optionally removing the water.

2. A process according to claim 1, wherein the reaction is conducted at a temperature of 40–50° C.

3. A process according to claim 1 further comprising conducting the reaction with a molar ratio of compound (III)/benzyl chloride of 1.6–2.0.

4. A process according to claim 3, further comprising conducting the reaction with a molar ratio of compound (III)/benzyl chloride of 1.7–1.9.

5. A process according to claim 1, further comprising introducing the benzyl chloride into the solution of compound (III) over the course of 8–16 hours, and introducing the water to the solution of the compound (III) over the course of 2–6 hours, wherein the beginning of water introduction occurs when 10–80% of the benzyl chloride has been introduced.

6. A process according to claim 1, further comprising conducting the process in the presence of at least one stabilizer of methyl ether of hydroquinone, hydroquinone, 3,5-di-tert-butyl-4-hydroxytoluene, or a mixture thereof, optionally at a proportion of 200–2000 ppm, based on the final aqueous solution, and/or in the presence of at least one sequestering agent for metals, optionally a proportion of 10–100 ppm, based on the final aqueous solution.

7. An aqueous solution solely of compound (I), the concentration of compound (I) being from 50–75% by weight made by a process according to claim 1.

8. An aqueous solution of compounds (I) and (II), the composition of the aqueous solution being the following, for 100 parts by weight:

| | |
|---|---|
| compound (I): | from 10 to 70% by weight |
| compound(s) (II): | from 10 to 70% by weight |
| water: | from 20 to 80% by weight, made by the process according to claim 1. |

9. A homopolymer or copolymer containing units of monomer (I) and optionally at least one unit of monomer (II), wherein monomer (I) and monomer (II) are made by the process according to claim 1.

10. A process according to claim 6, wherein the agent for sequestering metals is diethylenetriaminepentaacetic acid, pentasodium diethylenetriaminepentaacetate, N-hydroxyethylethylenediaminetriacetic acid, or trisodium N-hydroxyethylethylenediaminetriacetate.

11. A process according to claim 1, wherein the solvent is the compound of formula (I).

12. A process according to claim 1, wherein the solvent is the compound of formula (II).

13. A process according to claim 1, wherein the solvent is the mixture of the compounds of formula (I) and (II).

* * * * *